United States Patent [19]
Nanaumi et al.

[11] Patent Number: 5,800,783
[45] Date of Patent: Sep. 1, 1998

[54] NOX SENSOR FOR EXHAUST GAS AND METHOD FOR PRODUCING SAME

[75] Inventors: Masaaki Nanaumi; Norihiro Ohta; Youichi Asano; Yoshiaki Takagi; Yoshikazu Fujisawa, all of Saitama, Japan

[73] Assignee: Honda Giken Kogyo Kabushiki Kaisha, Tokyo, Japan

[21] Appl. No.: 967,076

[22] Filed: Nov. 10, 1997

Related U.S. Application Data

[63] Continuation of Ser. No. 579,909, Dec. 28, 1995, abandoned.

[30] Foreign Application Priority Data

Nov. 8, 1995 [JP] Japan .................. 7-290217

[51] Int. Cl.$^6$ .................................................. G01H 27/04
[52] U.S. Cl. .................... 422/94; 422/83; 422/95; 422/98; 73/31.05; 73/31.06; 436/106; 436/116; 436/149; 436/152; 204/424; 204/425; 204/153.14; 501/134
[58] Field of Search .................. 422/83, 74, 95, 422/98; 73/31.05, 31.06; 436/106, 116, 149, 152, 167; 204/424, 425, 153.14; 501/134

[56] References Cited

U.S. PATENT DOCUMENTS

| | | | |
|---|---|---|---|
| Re. 33,980 | 6/1992 | Matsuura et al. | 422/98 |
| 3,948,813 | 4/1976 | Holcombe, Jr. et al. | 252/520 |
| 4,066,413 | 1/1978 | Segawa et al. | 23/254 |
| 4,099,922 | 7/1978 | Yasuda et al. | 23/254 E |
| 4,187,486 | 2/1980 | Takahashi et al. | 338/34 |
| 4,194,994 | 3/1980 | Baresel et al. | 252/518 |
| 4,260,978 | 4/1981 | Yasuda | 338/24 |
| 4,351,182 | 9/1982 | Schmidberger | 73/27 R |
| 4,453,397 | 6/1984 | Ohta et al. | 73/23 |
| 4,456,902 | 6/1984 | Komine et al. | 338/34 |
| 4,458,233 | 7/1984 | Komine et al. | 338/34 |
| 4,542,640 | 9/1985 | Clifford | 73/23 |
| 4,652,849 | 3/1987 | Matsuura et al. | 338/34 |
| 4,661,234 | 4/1987 | Takehashi et al. | 204/406 |
| 4,668,635 | 5/1987 | Forster | 436/134 |
| 4,857,275 | 8/1989 | Furusaki et al. | 422/98 |
| 5,051,718 | 9/1991 | Satake et al. | 338/34 |
| 5,389,340 | 2/1995 | Satake | 422/98 |
| 5,397,442 | 3/1995 | Wachsman | 204/153.16 |
| 5,582,809 | 12/1996 | Rikimaru et al. | 423/239.1 |

FOREIGN PATENT DOCUMENTS

| | | |
|---|---|---|
| 6275244 | 4/1987 | Japan . |
| 1150849 | 6/1989 | Japan . |

OTHER PUBLICATIONS

Ishihara et al. Selective Detection of Nitrogen Monoxide by the Mixed Chromium–Niobium Oxide of $Cr_2O_3$ –$Nb_2O_5$. Chem. LcH (1988), 6, 997–1000.

English Abstract of JP 62-75244.

*Primary Examiner*—Jill Warden
*Assistant Examiner*—Sharidan Carrillo
*Attorney, Agent, or Firm*—Lyon & Lyon LLP

[57] ABSTRACT

An NOx sensor for an exhaust gas is made from $\beta\text{-}Nb_2O_5$ as a primary component and $TiO_2$ as a subsidiary component. The $TiO_2$ content is in a range of 0.1% by weight $\leq TiO_2 \leq$ 20% by weight. In place of $TiO_2$, Ru may be used in the NOx sensor. The Ru content is in a range of 0.1% by weight $\leq Ru \leq$ 10% by weight. Thus, the NOx sensor has an excellent NOx adsorbing ability and is higher in sensitivity to NOx in an exhaust gas.

15 Claims, 17 Drawing Sheets ary component and $TiO_2$ as a subsidiary component, the $TiO_2$ content being in a range of 0.1% by weight $\leq TiO_2 \leq 20\%$ by weight.

NOX SENSOR FOR EXHAUST GAS AND METHOD FOR PRODUCING SAME

This is a Continuation application, or of application Ser. No. 08/579,909 filed on Dec. 28, 1995, now abandoned.

BACKGROUND OF THE INVENTION

1. Field of the Invention

The present invention relates to an NOx (nitrogen oxides) sensor for an exhaust gas, which is used in a vehicle and the like.

2. Description of the Related Prior Art

There is a conventionally known a semiconductor NOx sensor made mainly using metal oxide (for example, see Japanese Patent Application Laid-open No. 150849/89). The measurement of NOx concentration by this semiconductor NOx sensor is carried out based on the fact that if NOx in exhaust gas is adsorbed to the metal oxide, the electric resistance value (which will be referred to as a resistance value hereinafter) of the metal oxide is varied.

Although, the semiconductor NOx sensor has an advantage in that it has a high in water resistance and is small-sized and inexpensive, there is a problem that it has a relatively low sensitivity to NOx and thus is not practical. Therefore, an improvement in this respect has been desired.

SUMMARY OF THE INVENTION

It is an object of the present invention to provide an NOx sensor for an exhaust gas, which is of a invention, there is provided an NOx sensor for an exhaust gas, comprising $\beta$-$Nb_2O_5$ as a primary component and $TiO_2$ as a subsidiary component, the $TiO_2$ content being in a range of 0.1% by weight $\leq TiO_2 \leq 20\%$ by weight.

In this NOx sensor, the $\beta$-$Nb_2O_5$ has a high sensitivity to NOx in an exhaust gas, but has a relatively high sensitivity even to $O_2$.

Therefore, a particular amount of $TiO_2$ is contained as the subsidiary component. Thus, the sensitivity of the NOx sensor to NOx can be further enhanced, and the sensitivity of the NOx sensor to $O_2$ can be lowered.

This is believed to be due to the following reason:

If a particular amount of $TiO_2$ is contained in the $\beta$-$Nb_2O_5$, predetermined $TiO_2$ is exposed on the surface of the $\beta$-$Nb_2O_5$ in a dotted manner. Thus, NOx in the exhaust gas is efficiently absorbed to the $TiO_2$, and overflows from the $TiO_2$, namely, a spill-over phenomenon is generated, whereby the overflowing NOx is absorbed to the surface of the $\beta$-$Nb_2O_5$ layer.

NOx in the exhaust gas is absorbed to the surface of the $\beta$-$Nb_2O_5$ layer by an effect of the $\beta$-$Nb_2O_5$ layer, and an semiconductor type and has a high sensitivity of NOx in an exhaust gas and is also practical.

To achieve the above object, according to the present invention, there is provided an NOx sensor for an exhaust gas, which is made of $\beta$-$Nb_2O_5$.

In the NOx sensor, the $\beta$-$Nb_2O_5$ is highly active and has an excellent NOx adsorbing ability and hence, has a high sensitivity to NOx in an exhaust gas.

The measurement of NOx concentration is carried out by the following process: If NOx is adsorbed to a surface of the $\beta$-$Nb_2O_5$ layer, the NOx exhibits an electron attracting effect, thereby electrons which are carriers of the $\beta$-$Nb_2O_5$ (n-type semiconductor) are attracted to NOx and hence, the resistance value of the $\beta$-$Nb_2O_5$ layer is increased. This resistance value is measured and converted into an NOx concentration. Therefore, in order to accurately measure the NOx concentration, it is important that the $\beta$-$Nb_2O_5$ has an excellent NOx absorbing ability.

It is another object of the present invention to provide an NOx sensor for an exhaust gas, which is of a semiconductor type and has a high sensitivity to NOx in an exhaust gas and a low sensitivity to other gases and also has a utility.

To achieve the above object, according to the present amount of NOx produced by the spill-over phenomenon is added to the amount of NOx adsorbed to the surface of the $\beta$-$Nb_2O_5$ layer. Therefore, the amount of NOx adsorbed is substantially increased, as compared with the NOx sensor made using only $\beta$-$Nb_2O_5$. If $TiO_2$ is used in combination with the $\beta$-$Nb_2O_5$ in the above manner, the sensitivity of the NOx sensor to NOx is enhanced.

In the nature of things, $O_2$ in the exhaust gas should be adsorbed intrinsically at a certain proportion to the surface of the $\beta$-$Nb_2O_5$ layer. But the $O_2$ adsorbing site is occupied by NOx which overflowed by the spill-over phenomenon. For this reason, the amount of $O_2$ adsorbed to the surface of the $\beta$-$Nb_2O_5$ layer is decreased, as compared with the NOx sensor made using only $\beta$-$Nb_2O_5$. If $TiO_2$ is used in combination with the $\beta$-$Nb_2O_5$ in the above manner, the sensitivity of the NOx sensor to $O_2$ is lowered.

In the measurement of NOx concentration, The $TiO_2$ exists in a dotted manner in the $\beta$-$Nb_2O_5$ layer and hence, does not vary the resistance value of the $\beta$-$Nb_2O_5$ layer.

However, if the content of $TiO_2$ is smaller than 0.1% by weight, or larger than 20% by weight, the sensitivity of the NOx sensor to NOx is lowered, and the sensitivity of the NOx sensor to $O_2$ is increased.

Even if Ru is used in place of $TiO_2$ in the NOx sensor, a spill-over phenomenon can likewise be generated, thereby enhancing the sensitivity of the NOx sensor to NOx and lowering the sensitivity of the NOx sensor to $O_2$. In this case, the Ru content is set in a range of 0.1% by weight $\leq Ru \leq 10\%$ by weight.

However, if the Ru content is smaller than 0.1% by weight, or larger than 10% by weight, the sensitivity of the NOx sensor to NOx is lowered, and the sensitivity of the NOx sensor to $O_2$ is increased.

The NOx sensor has a nature that if the concentration of the exhaust gas is lowered, the amounts of NOx, $O_2$ and the like are decreased, and if the temperature of the exhaust gas is lowered, the amounts of NOx, $O_2$ and the like adsorbed are increased.

The above and other objects, features and advantages of the invention will become apparent from the following description of preferred embodiments taken in conjunction with the accompanying drawings.

DESCRIPTION OF THE PREFERRED EMBODIMENTS (First Embodiment)

Figure 1:
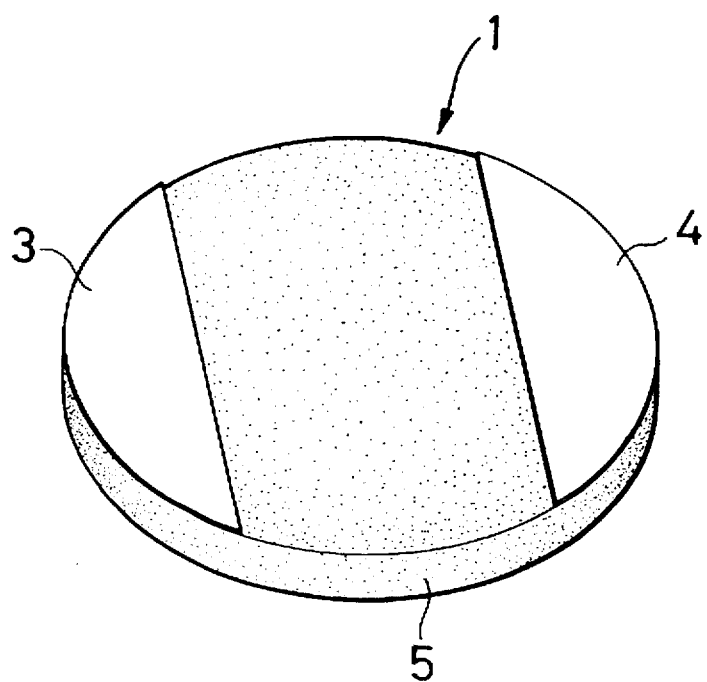
FIG. 1 is a perspective view of an NOx measuring element.

Referring to FIG. 1, an NOx measuring element 1 includes a semiconductor NOx sensor 5 having a tablet-like shape, and a pair of Pt thin film-like electrodes 3 and 4 deposited on a surface of the NOx sensor 5. A heater is provided on a back of the NOx sensor 5. The electrodes 3 and 4 are connected to a power source through a multi-meter. The NOx sensor 5 is a sinter made of $\beta\text{-}Nb_2O_5$.

Such NOx measuring element 1 was produced using a process described below.

(a) Ethanol was added to $\alpha\text{-}Nb_2O_5$ (made by Soekawa Chemicals Co., Ltd.) having a purity of 99.9% and then, using a planetary ball mill, the $\alpha\text{-}Nb_2O_5$ was pulverized for 3 hours at 300 rpm.

(b) The resulting $\alpha\text{-}Nb_2O_5$ powder was subjected to a pressing for 5 minutes at 400 $kfg/cm^2$ to form a tablet having a diameter of 10 mm and a thickness of 3 mm.

(c) The tablet was subjected to a sintering for 4 hours at 1,000° C. to provide a tablet-like NOx sensor 5 of $\beta\text{-}NO_2O_5$. In this case, the $\alpha\text{-}Nb_2O_5$ (a rhombic crystal) is transformed into $\beta\text{-}Nb_2O_5$ (a monoclinic crystal) at about 900° C.

(d) Electrodes 3 and 4 were formed by depositing Pt on a surface of the NOx sensor 5 by utilizing a sputtering process, thereby producing an NOx measuring element 1. This NOx measuring element 1 is called an example 1.

NOx measuring elements 1 of $\beta\text{-}Nb_2O_5$ were produced under the same conditions in the above-described producing process, except that the sintering temperature was changed to 900° C. and 1,110° C. The NOx measuring element 1 produced at the sintering temperature of 900° C. is called an example 2, and the NOx measuring element 1 produced at the sintering temperature of 1,100° C. is called an example 3.

For composition, an NOx measuring element 1 of $\alpha\text{-}Nb_2O_5$ was produced under the same conditions in the above-described producing process, except that the sintering temperature was set at 800° C. This NOx measuring element 1 is called an example 4.

Using the examples 1 and 4 of the NOx measuring elements 1, the measurement of a sensitivity to NOx (in this case, NO and sic passim throughout the preferred embodiments) which will be described below was carried out.

First, the NOx measuring element 1 heated to 450° C. by a heater was placed into an $N_2$ atmosphere having a temperature of 450° C., and an initial resistance $R_N$ was measured using the multi-meter. Then, the NOx measuring element 1 heated to 450° C. by the heater was placed into an atmosphere comprising 3000 ppm of NOx and the balance of $N_2$ and having a temperature of 450° C., and a resistance value $R_{NO}$ was measured using the multi-meter.

A sensitivity of the NOx sensor 5 to NOx was calculated according to the following equation:

NOx sensitivity (%)=$\{(R_{NO}-R_N)/R_N\}\times 100$

Figure 2:
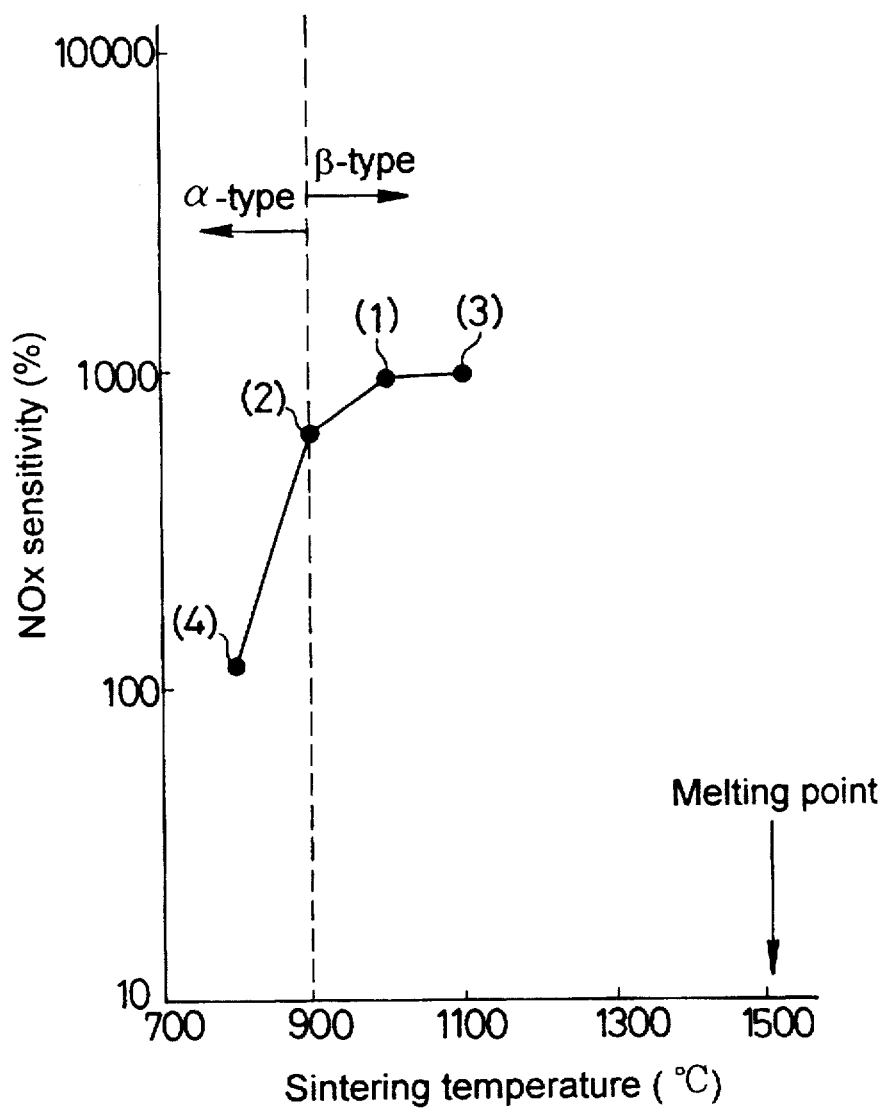
FIG. 2 is a graph illustrating the relationship between the sintering temperature and the NOx sensitivity.

FIG. 2 is a graph illustrating the NOx sensitivity of the examples 1 to 4. In FIG. 2, points 1 to 4 correspond to the examples 1 to 4, respectively. As is apparent from FIG. 2, the examples 1 to 3 each having the NOx sensor 5 of $\beta\text{-}Nb_2O_5$ are higher in sensitivity to NOx, as compared with the example 4 having the NOx sensor 5 of $\alpha\text{-}Nb_2O_5$. This is believed to be for a reason which will be described below. The $\beta\text{-}Nb_2O_5$ is highly active, and has an excellent adsorbing ability to NOx, as compared with $\alpha\text{-}Nb_2O_5$. The $\alpha\text{-}Nb_2O_5$ is a granular crystal and even if the $\alpha\text{-}Nb_2O_5$ is sintered, a large number of pores exist in a granular crystal aggregate. On the contrast, the $\beta\text{-}Nb_2O_5$ is a needle crystal, and when the $\alpha\text{-}Nb_2O_5$ is transformed into the $\beta\text{-}Nb_2O_5$, adjacent needle crystals are in close contact with each other. For this reason, the number of pores existing in the needle crystal aggregate is substantially smaller than that in the granular crystal aggregate. Thus, a flow of electrons in the NOx sensor 5 of $\beta\text{-}Nb_2O_5$ is more smooth than that in the NOx sensor 5 of $\alpha\text{-}Nb_2O_5$.

Then, using the example 1 of the NOx measuring element 1, the NOx sensitivity of the NOx sensor 5 was examined under the same conditions as those described above, except that the NOx concentration was varied, thereby was added thereto provide a liquid mixture.

(b) Pure water was dropped in an amount of 28 ml into the liquid mixture, while agitating the liquid mixture, thereby providing a mixture comprising -Nb and Ti oxides and hydroxides.

(c) The mixture was subjected to a drying at 100° C. for 2 hours and then to a firing at 500° C. for 30 minutes to provide an oxide mixture comprising $\alpha\text{-}Nb_2O_5$ and 0.5 weight % of $TiO_2$.

(d) 60 g of the oxide mixture and 40 g of a solution of ethyl-cellulose to α-terpeneol are mixed together to provide a printing paste.

(e) A screen printing was conducted using the paste on the base plate 2 having the pair of electrode 3 and 4 so as to cover the comb-like portions 3a and 4a, thereby forming a thin film-like member.

(f) The base plate 2 having the thin film-like member was subjected to a stepwise sintering at 150° C. for 30 minutes, at 400° C. for 30 minutes, at 800° C. for 2 hours and at 1,000° C. for 4 hours, thereby producing an NOx measuring element 1 having an NOx sensor 5 made from $\beta\text{-}Nb_2O_5$ and $TiO_2$. This NOx measuring element 1 is called an example 1.

Figure 3:
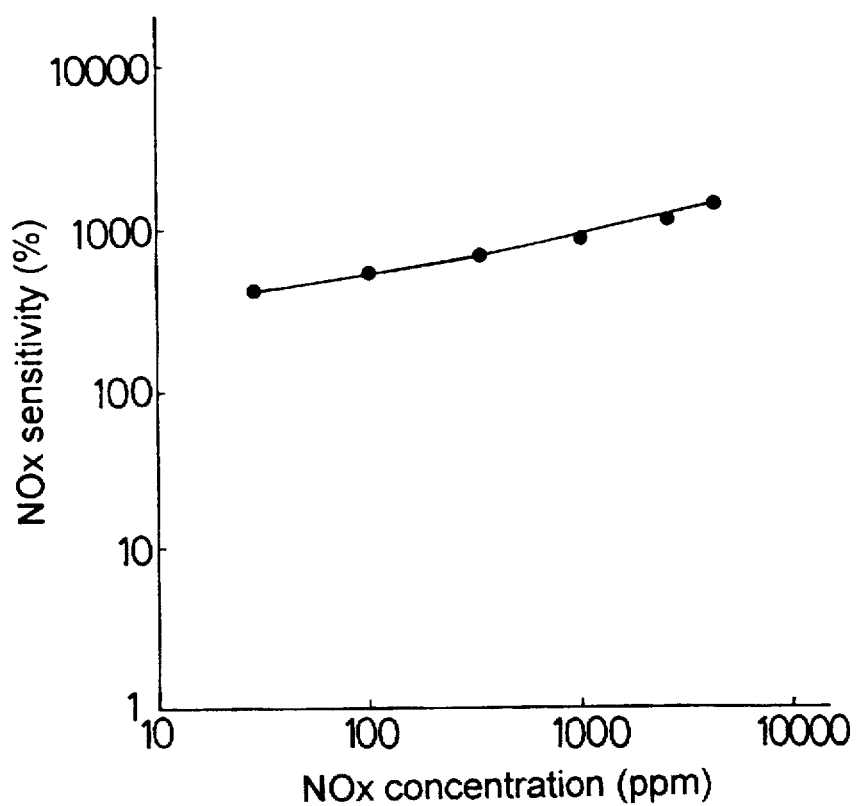
FIG. 3 is a graph illustrating the relationship between the NOx concentration and the NOx sensitivity.

Using, as a printing paste, a mixture of 40 g of a providing results shown in FIG. 3. As is apparent from FIG. 3, the NOx sensitivity is increased as the NOx concentration is increased.

(Second Embodiment)

Figure 4:
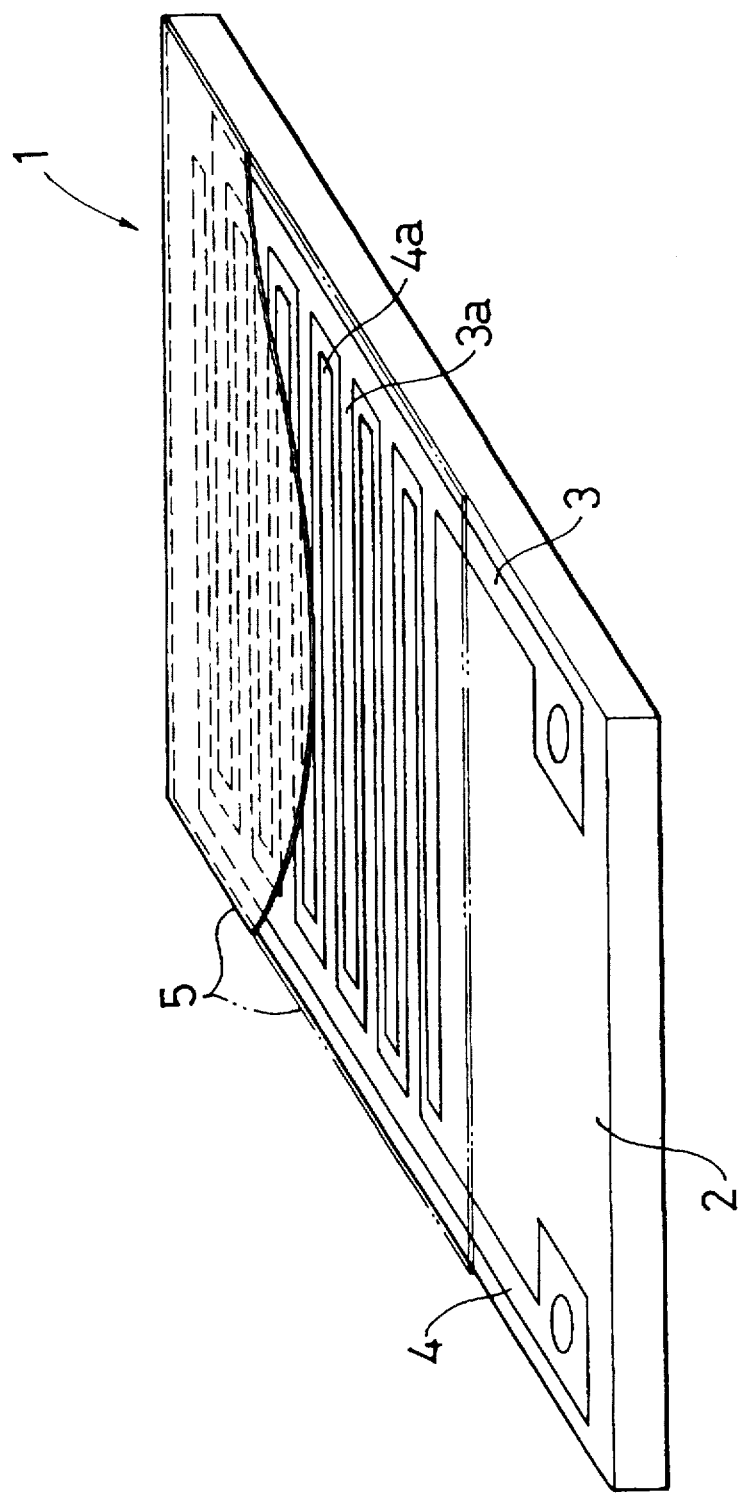
FIG. 4 is a perspective view of an NOx measuring element.

Referring to FIG. 4, an NOx measuring element 1 includes a base plate 2 made of $Al_2O_3$, a pair of thin film-like electrodes 3 and 4 made of Pt and deposited on the surface of the base plate 2, and a thin film-like semiconductor NOx sensor 5 deposited on comb-like portions 3a and 4a of the electrodes 3 and 4 and on the base plate 2 to cover the comb-like portions 3a and 4a. The thin film-like electrodes 3 and 4 are deposited on the surface of the base plate 2 such that the comb-like portions 3a and 4a are mashed with each other. A heater is provided on a back of the base plate 2. The electrodes 3 and 4 are connected to a power source through a multi-meter. The NOx sensor 5 is made from 99.5% by weight of $\beta$-$Nb_2O_5$ and 0.5% by weight of $TiO_2$.

Such NOx measuring element 1 was produced using the following process.

(a) 50 g of dehydrated ethanol was added to 12.5 g of niobium ethoxide [-$NO(OC_2H_5)_5$] (made by Chemicals Co., Ltd.) and then, 74 mg of titanium ethoxide [$Ti(OC_2H_5)_5$] (made by Soekawa Chemicals Co., Ltd.) solution of ethylcellulose in $\alpha$-terpeneol and 60 g of $\alpha$-$Nb_2O_5$ powder made by pulverizing $\alpha$-$Nb_2O_5$ (made by Soekawa Chemicals Co., Ltd.) having a plurality of 99.9% for 3 hours by using a planetary ball mill, a screen printing and a sintering similar to those described above were conducted to provide an NOx measuring element made of $\alpha$-$Nb_2O_5$ converted into $\beta$-type. This NOx measuring element is called an example 2.

Using the examples 1 and 2 of the NOx measuring elements 1, the measurement of a sensitivity to NOx and $O_2$ was carried out in the following manner.

First, the NOx measuring element 1 heated to 450° C. by a heater was placed into an $N_2$ atmosphere having a temperature of 450° C. to measure an initial resistance $R_N$ by use of the multi-meter. Then, the NOx measuring element 1 heated to 450° C. was placed into an atmosphere comprising 1,000 ppm of NOx and the balance of $N_2$ and having a temperature of 450° C. as well as into an atmosphere comprising 2% by volume of $O_2$ and the balance of $N_2$ and having a temperature of 450° C. to measure a resistance $R_{NO}$ in the atmosphere containing NOx and a resistance $R_O$ in the atmosphere containing $O_2$ by use of the multi-meter.

The sensitivity of the NOx sensor 5 to the NOx and $O_2$ was calculated according to the following equations:

NOx sensitivity (%)={$(R_{NO}-R_n)/R_N$}×100

$O_2$ sensitivity (%)={$(R_O-R_N)/R_N$}×100

Figure 5:
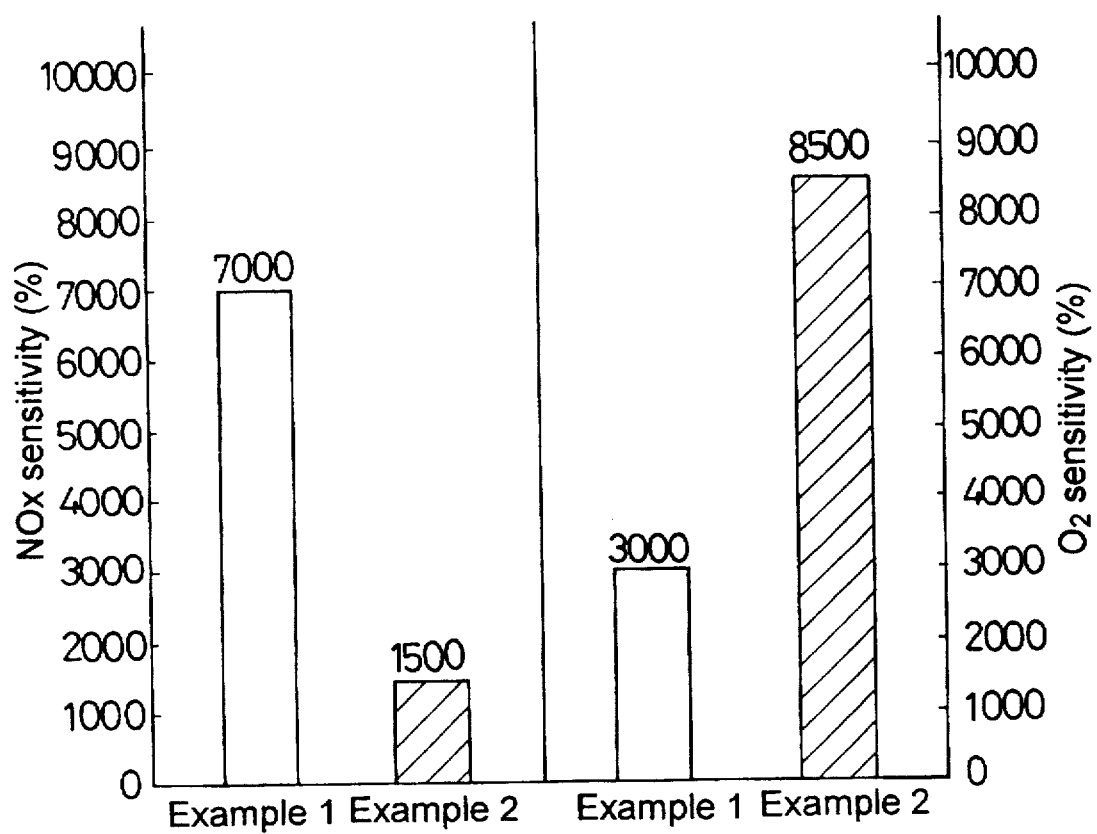
FIG. 5 is a graph illustrating the relationship between the sensitivity of the NOx sensor to NOx and the sensitivity of the NOx sensor to $O_2$.

FIG. 5 is a graph illustrating the NOx sensitivity and the $O_2$ sensitivity of the examples 1 and 2. As is apparent from FIG. 5, the example 1 having the NOx sensor 5 containing $\beta$-$Nb_2O_5$ and 0.5% by weight of $TiO_2$ is higher in sensitivity to NOx and lower in sensitivity to $O_2$, as compared with the example 2 having the NOx sensor made of only $\beta$-$Nb_2O_5$.

Various NOx measuring elements 1 were produced in the same process, except that the content of $TiO_2$ in the NOx sensor 5 was varied. Using these NOx measuring elements 1, the measurement of a sensitivity to NOx and to $O_2$ was carried out under the same conditions as those described above, thereby providing results shown in FIG. 6.

Figure 6:
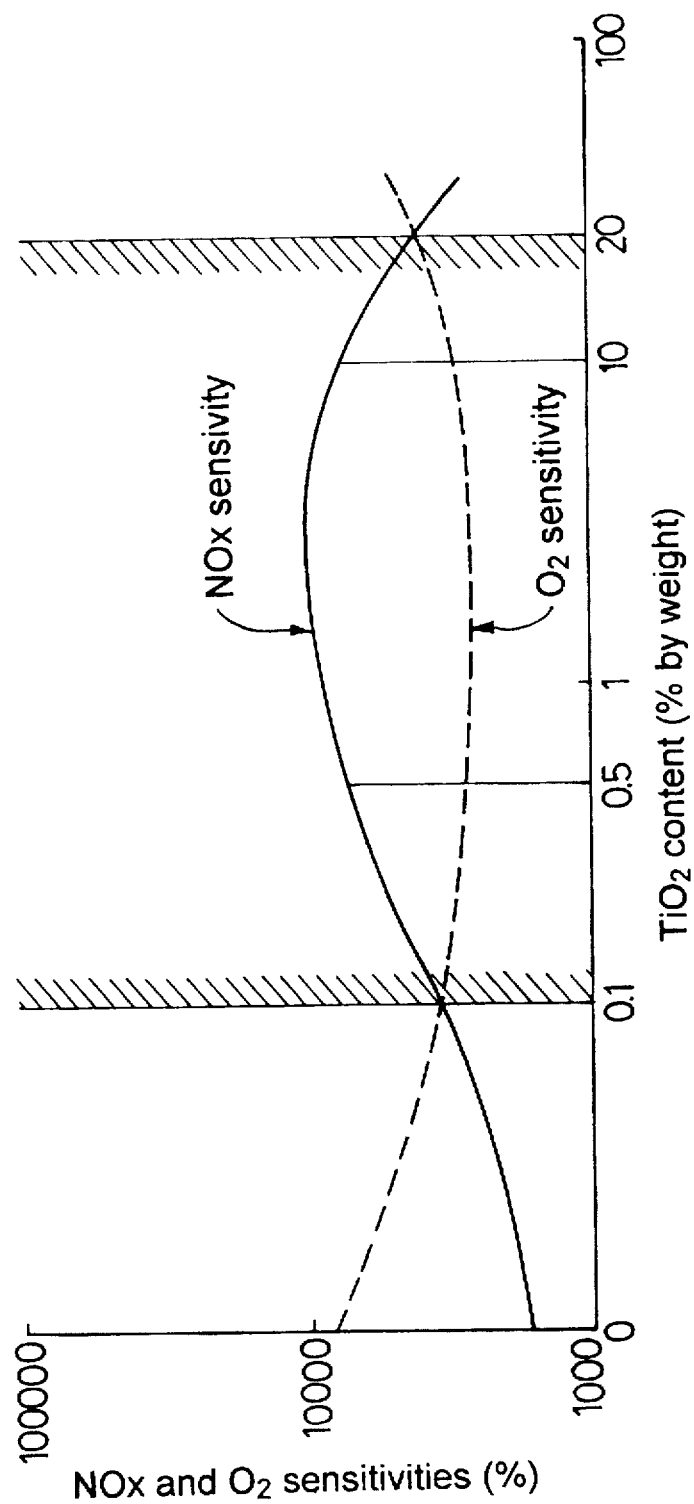
FIG. 6 is a graph illustrating the relationship between the $TiO_2$ content and the NOx and $O_2$ sensitivities.

As is apparent from FIG. 6, if the content of $TiO_2$ is set in a range of 0.1% by weight $\leq TiO_2 \leq 20\%$ by weight, the NOx sensitivity and the $O_2$ sensitivity can be made equal to each other, or the NOx sensitivity can be made high, and the $O_2$ sensitivity $R_O$ can be made low. Preferably, the content of $TiO_2$ is in a range of 0.5% by weight $\leq TiO_2 \leq 10\%$ by weight. By setting the content in this range, the NOx sensitivity can be made extremely high, the $O_2$ sensitivity is extremely low.

Supposing concentrations of NOx, CO and HC (propylene) at an air-fuel ratio A/F equal to 22, first, second and third gases for test given in Table 1 were prepared.

TABLE 1

|  |  | Constituents (ppm) | | | |
| --- | --- | --- | --- | --- | --- |
|  |  | NOx | CO | HC | $N_2$ |
| A/F = 22 | First gas | 310 | — | — | balance |
|  | Second gas | — | 900 | — | balance |
|  | Third gas | — | — | 900 | balance |

Figure 7:
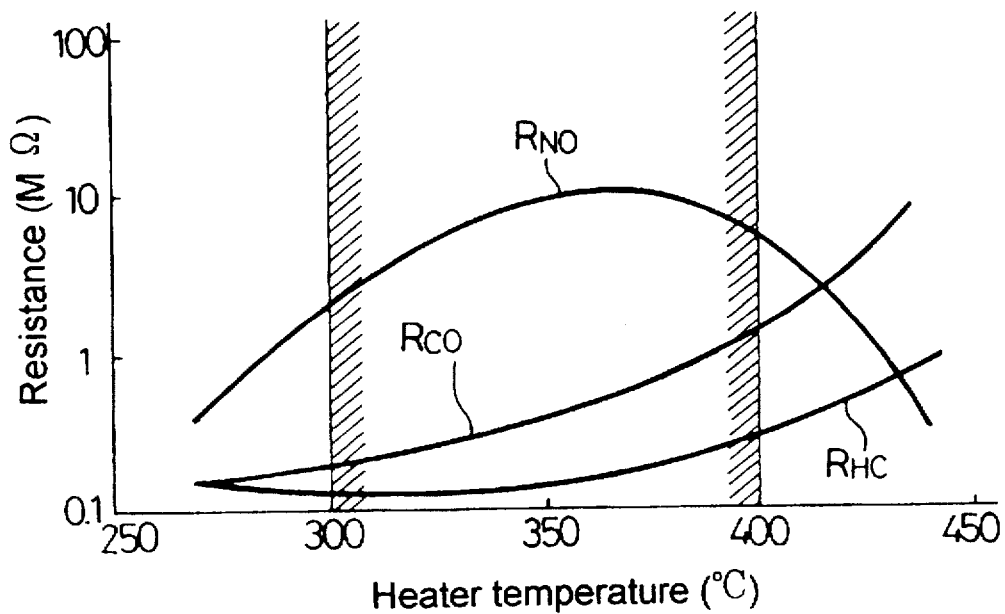
FIG. 7 is a graph illustrating the relationship between the heater temperature and the sensitivities to various gases.

The NOx measuring element 1 including the NOx sensor 5 having a content of $TiO_2$ equal to 0.5% by weight was placed into each of the first, second and third cases maintained at various temperatures to measure NOx, CO and HC sensitivities $R_{NO}$, $R_{CO}$ and $R_{CH}$ in terms of resistance values, thereby providing the results shown in FIG. 7. In this case, the temperature provided by the heater of the NOx measuring element 1 is the same as the gas temperature.

As is apparent from FIG. 7, it can be seen that the NOx sensitivity $R_{NO}$ of the NOx sensor 5 is increased, while the CO and HC sensitivities $R_{CO}$ and $R_{CH}$ are decreased by maintaining the heater temperature T in a range of 300° C.$\leq T \leq$400° C. at a air-fuel ratio A/F equal to 22. Therefore, it is preferable that the heater temperature T is maintained in such range.

Figure 8:
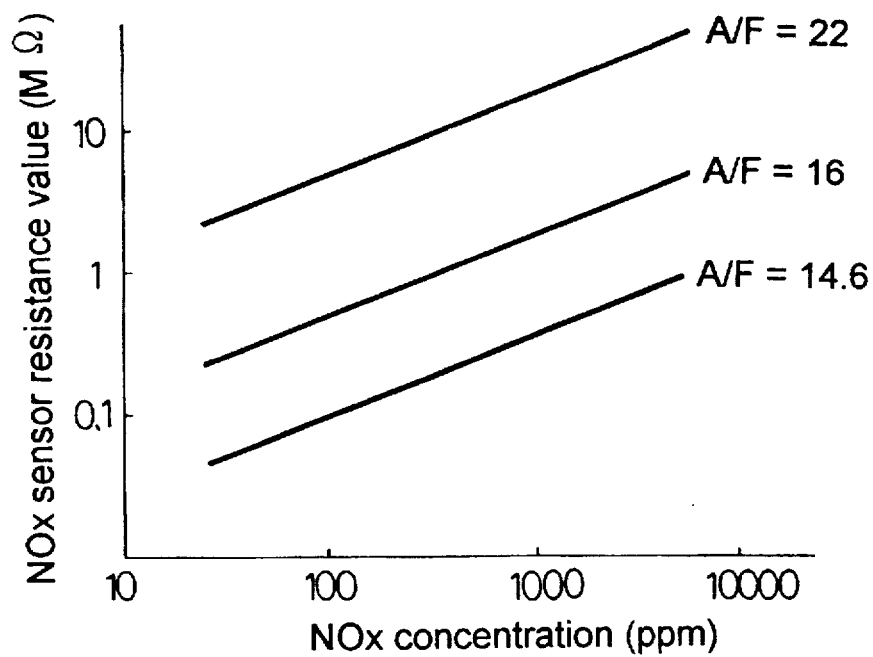
FIG. 8 is a graph illustrating the relationship between the NOx concentration and the resistance value of the NOx sensor.

FIG. 8 illustrates the relationship between the NOx concentration and the resistance value of the NOx sensor 5 at an air-fuel ratio A/F equal to 14.6, 16 and 22. Table 2 shows the air-fuel ratio A/F and the $O_2$ concentration (general values).

TABLE 2

| Air-fuel ratio A/F | 14.6 | 16 | 18 | 22 |
| --- | --- | --- | --- | --- |
| $O_2$ concentration (% by weight) | 0.5 | 1.9 | 4.3 | 8.0 |

As is apparent from FIG. 8 and Table 2, if the NOx concentration is increased, the resistance value of the NOx sensor 5 is increased due to an influence of the corresponding $O_2$ concentration at each air-fuel ratio A/F. At the same NOx concentration, if the air-fuel ratio A/F is increased, namely, if the $O_2$ concentration is increased, the resistance value of the NOx sensor 5 is increased to an extent corresponding to the $O_2$ concentration.

In order to accommodate such a phenomenon, the $O_2$ concentration corresponding to the air-fuel ratio A/F is measured, a resistance value of the NOx sensor 5 corresponding to the $O_2$ concentration is calculated, and the resistance value is subtracted from a measured resistance value. Thus, it is possible to determine a highly accurate NOx sensitivity $R_{NO}$.

Figure 9:
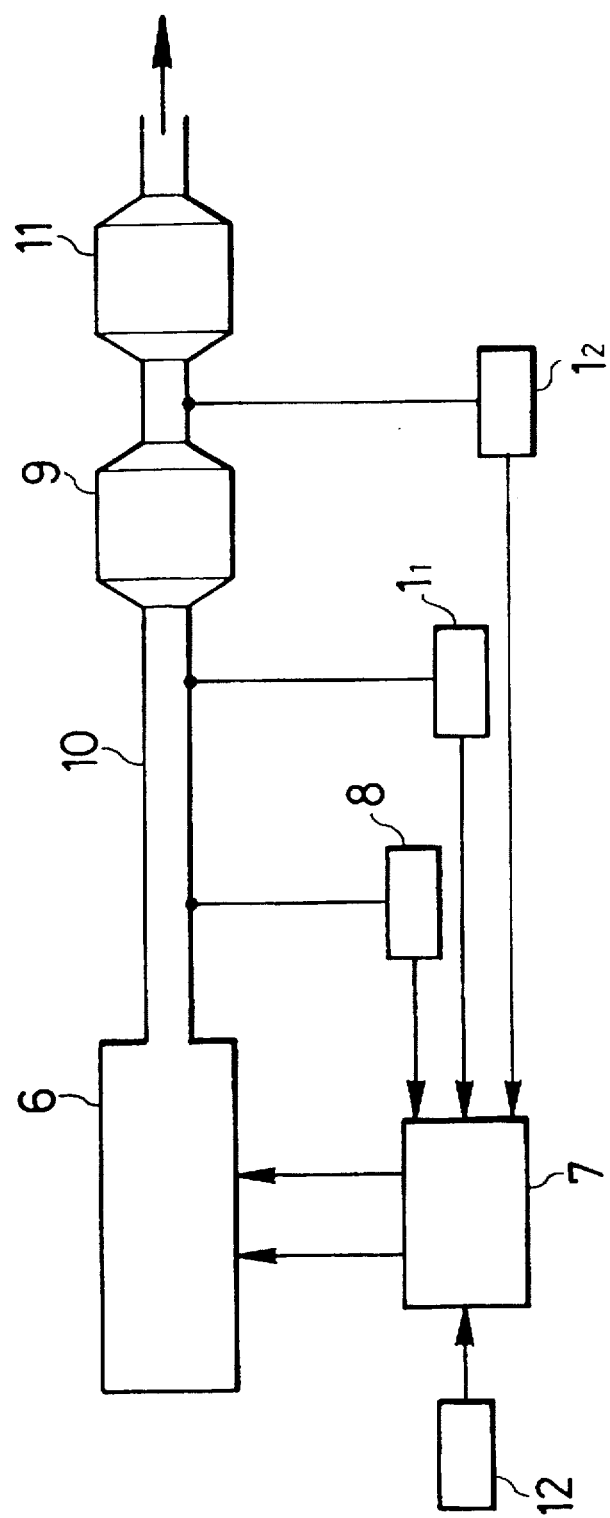
FIG. 9 is a block diagram illustrating an NOx purifying system.

The correction of the NOx sensitivity by measurement of the $O_2$ concentration can be carried out using an output (A/F value) from a limiting current type $O_2$ sensor (LAF sensor) in a vehicle including a lean burn engine 6 and an electronic injection device 7 shown in FIG. 9.

In this case, a first NOx measuring element $1_1$ is disposed to an upstream portion of an exhaust pipe 10 of an NOx occluding agent 9, and a second NOx measuring element $1_2$ is disposed to the exhaust pipe 10 between the NOx occluding agent 9 and a ternary catalyst 11. The second NOx measuring element $1_2$ may be disposed in the exhaust pipe 10 downstream from the ternary catalyst 11. In FIG. 9, reference character 12 is a sensor for detecting a number of revolutions of the engine. An NOx purifying system including the first and second NOx measuring elements $1_1$ and $1_2$ and the like will be described hereinafter.

Figure 10:
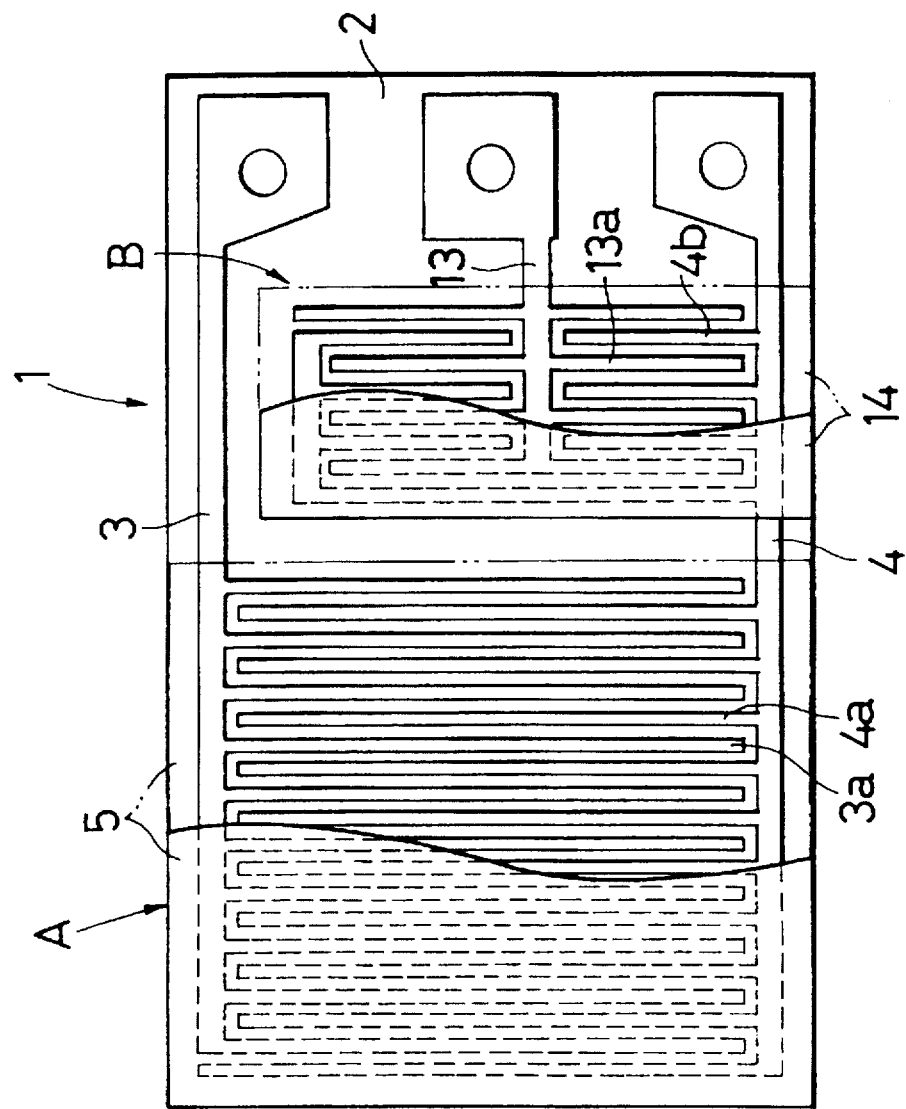
FIG. 10 is a plan view of an NOx measuring element.

FIG. 10 shows a modification to the NOx measuring element 1. This NOx measuring element 1 includes an NOx measuring element area A having the same structure as that described above, and a correcting $O_2$ measuring element area B.

The correcting $O_2$ measuring element area B includes a base plate 2 made of $Al_2O_3$ common to the NOx measuring element area A, a pair of thin film-like electrodes 4 and 13 which are deposited on a surface of the base plate 2 with their comb-like portions 4b and 13a disposed so as to be meshed with each other, and a thin film-like semiconductor $O_2$ sensor 14 deposited on the comb-like portions 4b and 13a and the base plate 2 to cover comb-like portions 4b and 13a. The electrode 4 is common to the NOx measuring element area A. A heater is provided on a back of the base plate 2.

If such NOx measuring element 1 is used, the NOx sensitivity can be corrected by $O_2$ sensitivity to determine a highly accurate NOx sensitivity.

The $O_2$ sensor 14 is an oxide mixture of 99.5% by atom of $\beta\text{-Nb}_2O_5$ and 0.5% by atom of Cu.

The $O_2$ measuring element area B and thus, the $O_2$ measuring element B (for convenience, the same reference character is used) was produced using a process which will be described below.

(a) Dehydrated ethanol was added to niobium ethoxide [-Nb(OC$_2$H$_5$)$_5$] (made by Soekawa Chemicals Co., Ltd., and then, copper ethoxide [Cu(OC$_2$H$_5$)$_5$] (made by Soekawa Chemicals Co., Ltd.) was added to provide a liquid mixture.

(b) Pure water was dropped into the liquid mixture, while agitating the liquid mixture, and the resulting mixture was dried at 110° C. to provide powder.

(c) The powder was subjected to a drying at 100° C. for 2 hours and then to a sintering at 500° C. for 30 minutes to provide an oxide mixture comprising $\alpha\text{-Nb}_2O_5$ and 0.5% by atom of Cu.

(d) 60 g of the oxide mixture and 40 g of solution of ethyl cellulose in $\alpha$-terpanenol were mixed together to provide a printing paste.

(e) The paste was subjected to a screen printing on the base plate 2 having the pair of electrodes 4 and 13, as shown in FIG. 10, thereby forming a thin film-like member.

(f) The base plate 2 having the thin film-like member was subjected to a stepwise sintering similar to that described above, thereby providing an $O_2$ measuring element B having an $O_2$ sensor 14 made of $\beta\text{-Nb}_2O_5$ and Cu. This $O_2$ measuring element B is called an example 1.

Using, as a printing paste, a mixture of 40 g of a solution of ethyl-cellulose in $\alpha$-terpenenol and 60 g of $\alpha\text{-Nb}_2O_5$ powder made by pulverizing $\alpha\text{-Nb}_2O_5$ (made by Soekawa Rikagaku Kabushiki Kaisha) having a purity of 99.9% for 3 hours by use of a planetary ball mill, a screen printing and a sintering similar to those described above were conducted to provide an $O_2$ measuring element made of $\text{-Nb}_2O_5$ converted into $\beta$-type. This $O_2$ measuring element B is called an example 2.

Using the examples 1 and 2 of the $O_2$ measuring elements B, the measurement of sensitivities to $O_2$ and NOx was carried out in the following manner.

First, the $O_2$ measuring element B heated to 450° C. by the heater was laced into an $N_2$ atmosphere having a temperature of 450° C. to measure an initial resistance $R_N$ by use of the multi-meter. Then, the $O_2$ measuring element B was placed into an atmosphere of a base gas comprising 500 ppm of NOx and the balance of $N_2$ was varied $O_2$ concentrations and maintained at 450° C. to measure a resistance value $R_O$ by use of the multi-meter.

The $O_2$ measuring element B was placed into an atmosphere of a base gas comprising 5% by volume of $O_2$ and the balance of $N_2$ with varied NOx concentrations and maintained at 450° C. to measure a resistance value $R_{NO}$ by use of the multi-meter.

The sensitivities of the NOx sensor 5 to NOx and $O_2$ were calculated according to the following equations:

$$O_2 \text{ sensitivity } (\%) = \{(R_O - R_N)/R_N\} \times 100$$

$$NOx \text{ sensitivity } (\%) = \{(R_{NO} - R_N)/R_N\} \times 100$$

Figure 11:
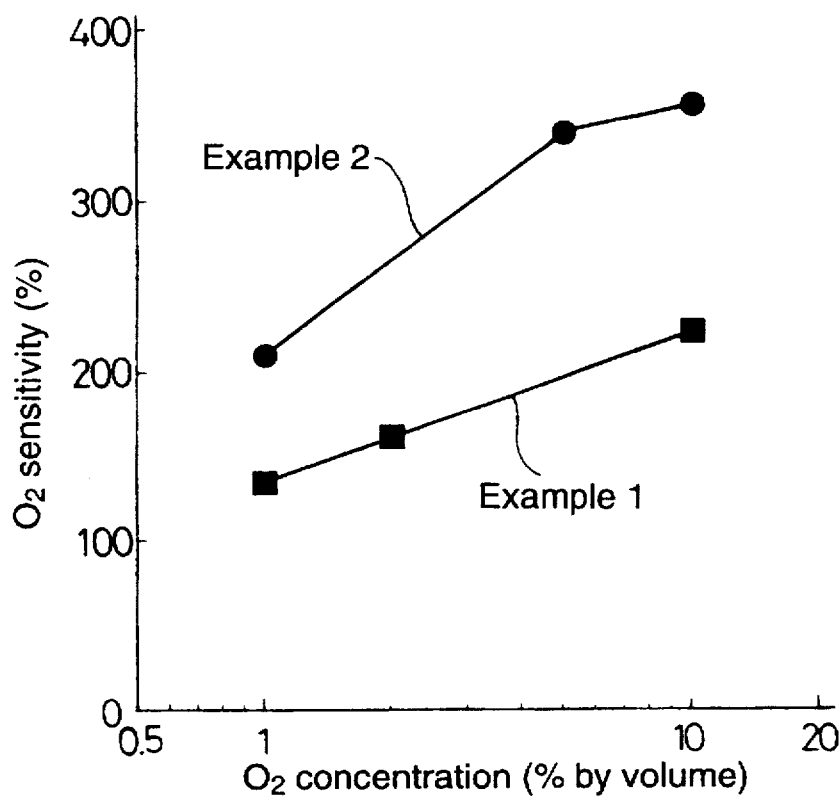
FIG. 11 is a graph illustrating the relationship between the $O_2$ concentration and the $O_2$ sensitivity.
Figure 12:
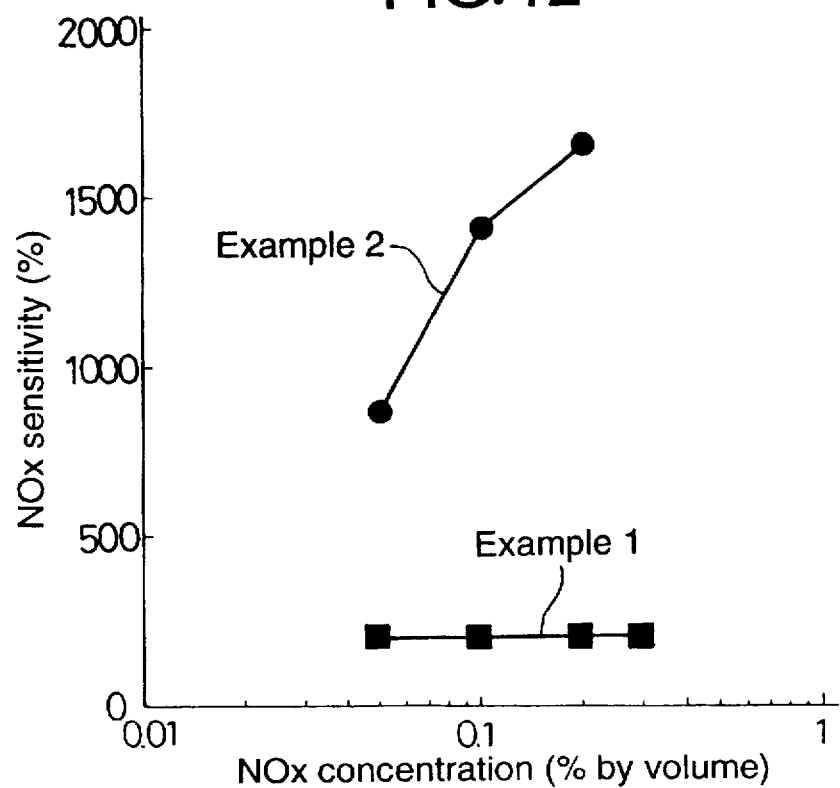
FIG. 12 is a graph illustrating the relationship between the NOx concentration and the NOx sensitivity.

FIG. 11 shows the $O_2$ sensitivity, and FIG. 12 shows the NOx sensitivity. As is apparent from FIGS. 11 and 12, if the example 1 having the $O_2$ sensor 14 containing $\beta\text{-Nb}_2O_5$ and 0.5% by atom of Cu is compared with the example 2 having the $O_2$ sensor made of only $\beta\text{-Nb}_2O_5$, the example 1 is relatively high in $O_2$ sensitivity and extremely low in NOx sensitivity. In this way, the example 1 is effective for use as an $O_2$ measuring element, because it is low in sensitivity to NOx which disturbs the measurement of $O_2$ concentration.

Then, various $O_2$ measuring elements B were produced by the same process as that described above, except that the content of Cu in the $O_2$ sensor 14 was varied. Using these $O_2$ measuring elements B, the measurement of sensitivities to $O_2$ and NOx was carried out under the same conditions as those described above to provide results shown in FIG. 13. The $O_2$ sensitivity and the NOx sensitivity are indicated by resistance values $R_O$ and $R_{NO}$, respectively.

Figure 13:
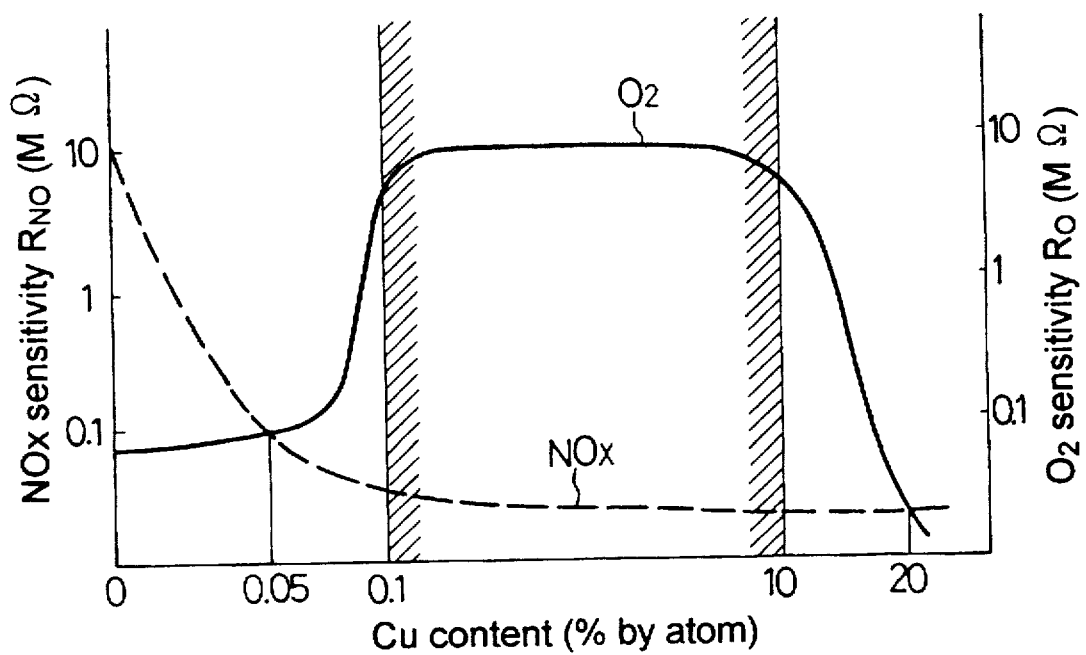
FIG. 13 is a graph illustrating the relationship between the Cu content and the NOx sensitivity as well as the $O_2$ sensitivity.

As is apparent from FIG. 13, if the Cu content is set in a range of 0.1% by atom $\leq Cu \leq 10\%$ by atom, an $O_2$ measuring element having a high $O_2$ sensitivity $R_O$ and an extremely low NOx sensitivity $R_{NO}$ can be produced.

It is believed that if a particular amount of Cu is contained in $\beta\text{-Nb}_2O_5$ in the above manner, the sensitivity of a resulting $O_2$ sensor to NOx is reduced, for example, because the absorbing characteristic of the $O_2$ sensor 14 is changed and the decomposition of NOx is caused by a catalytic effect of Cu in the $O_2$ sensor 14.

Figure 14:
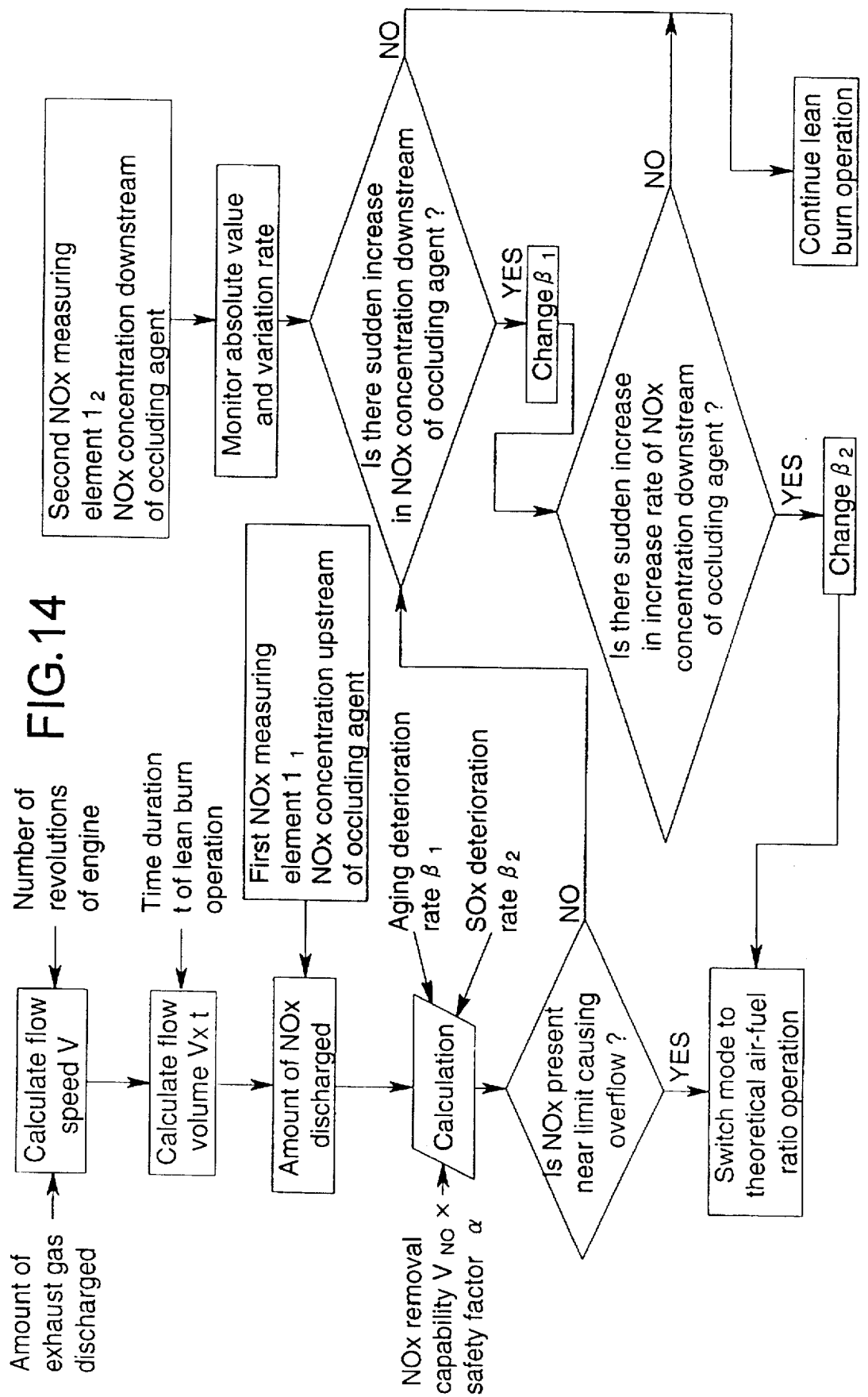
FIG. 14 is a flow chart for an NOx purifying system.

The NOx purifying system shown in FIG. 9 will be described with reference to the flow chart in FIG. 14.

(1) In a lean burn operation, a flow speed V of an exhaust gas is calculated from an exhaust gas amount and a number of revolutions of an engine.

(2) A flow volume V×t of the exhaust gas is calculated from the flow speed V of the exhaust gas and a duration time t of the lean burn operation.

(3) An amount of NOx discharged, i.e., $C_{NO} \times V \times t$ is calculated based an output from the first NOx measuring element $1_1$, wherein $C_{NO}$ is a concentration of NOx at a location upstream of the NOx occluding agent 9.

(4) An actual NOx adsorbing capability $V_{NO} \times \alpha \times (\beta_1 + \beta_2)$ of the NOx occluding agent 9 is calculated from an NOx adsorbing capability $V_{NO}$, a safety factor $\alpha$, an aging deterioration rate $\beta_1$ and an SOx deterioration rate $\beta_2$ in the NOx occluding agent 9.

Then, it is determined by calculation whether a relation, $V_{NO} \times \alpha \times (\beta_1 + \beta_2) > C_{NO} \times V \times t$ is established. In order to prevent an overflow of NOx from the NOx occluding agent 9, the left and right sides must be in an unequal relationship.

(5) When NOx is present near a limit causing an overflow, the mode is switched to a theoretical air-fuel ratio operation.

(6) An absolute value of and a variation rate in NOx concentration downstream of the NOx occluding agent 9 are monitored based on an output from the second NOx measuring element $1_2$.

(7) If the unequal relationship is established and if a sudden increase in NOx concentration downstream of the NOx occluding agent 9 is not produced, the lean burn operation is continued. If the sudden increase in NOx concentration is produced, the aging deterioration rate $\beta_1$ is changed, and the mode is switched to the theoretical air-fuel ratio operation.

(8) If the unequal relationship is established and if a sudden increase in increase rate of the NOx concentration downstream of the NOx occluding agent 9 is not produced, the lean burn operation is continued. If the sudden increase in increase rate of the NOx concentration is produced, the SOx deterioration rate $\beta_2$ is changed, and the mode is switched to the theoretical air-fuel ratio operation.

Figure 15:
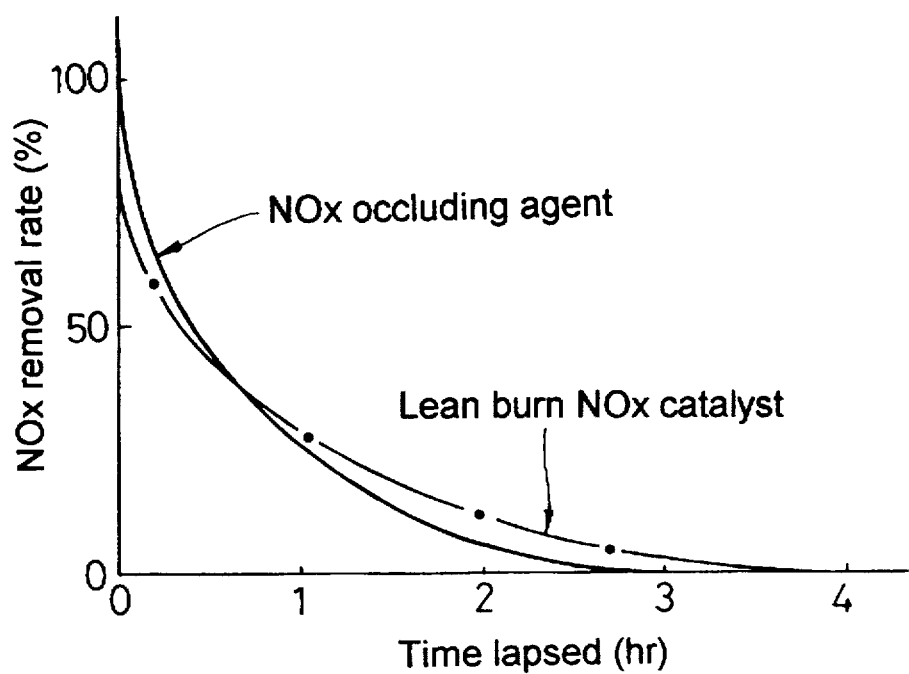
FIG. 15 is a graph illustrating the relationship between the time lapsed and the NOx removal rate.

A solid line in FIG. 15 indicates a deteriorated situation of the NOx occluding agent 9 due to SOx. The deterioration of the NOx occluding agent 9 was measured using a gas having a composition comprising 6% by volume of $H_2O$, 10% by volume of $O_2$, 500 ppm of NOx, 500 ppm of $C_3H_6$ and 10 to 100 ppm of SOx under conditions of a gas temperature of 450° C. and SV47000.

It can seen from the solid line in FIG. 15 that the NOx occluding agent 9 is deteriorated in a short time by SOx.

The amount of NOx in an exhaust gas is varied to a large extent depending upon the operation mode. In the prior art removal system including no NOx measuring element, it is necessary to conduct the lean burn operation to a value of an initial sudden-increase capability multiplied by a safety factor, so that NOx is prevented from flowing to the outside in any operational situation, and then to conduct the theoretical air-fuel ratio operation for a given time, thereby restoring the purifying performance in a reducing atmosphere.

In an actual case, the initial sudden-increase capability is multiplied by a safety factor which takes the deterioration (30 to 40% down) due to an aging into consideration and hence, the theoretical air-fuel ratio operation must be conducted at a fairly short cycle. In such a removal system, the lean burn operation is short, and there is a possibility that an essential low specific fuel consumption property peculiar to the lean burn is injured.

In the NOx purifying system shown in FIG. 9, the NOx measuring element $1_1$ is disposed upstream of the NOx occluding agent 9 to accumulatively calculate the amount of NOx discharged from the NOx concentration at a place upstream of the NOx occluding agent 9. Therefore, a timing for switching the mode to the theoretical air-fuel ratio operation can be predicted in advance.

The deterioration of NOx occluding agent 9 which gradually advances due to an aging can be perceived by monitoring the NOx concentration by the second NOx measuring element $1_2$ which is disposed downstream from the NOx occluding agent 9. It is also possible to perceive the timing for switching the mode to the theoretical air-fuel ratio operation by the NOx concentration. Especially, because the deterioration of the NOx occluding agent 9 by SOx poisoning occurs rapidly, as shown by a solid line in FIG. 15, it is extremely effective that the second NOx measuring element $1_2$ is disposed downstream from the NOx occluding agent 9.

Figure 16:
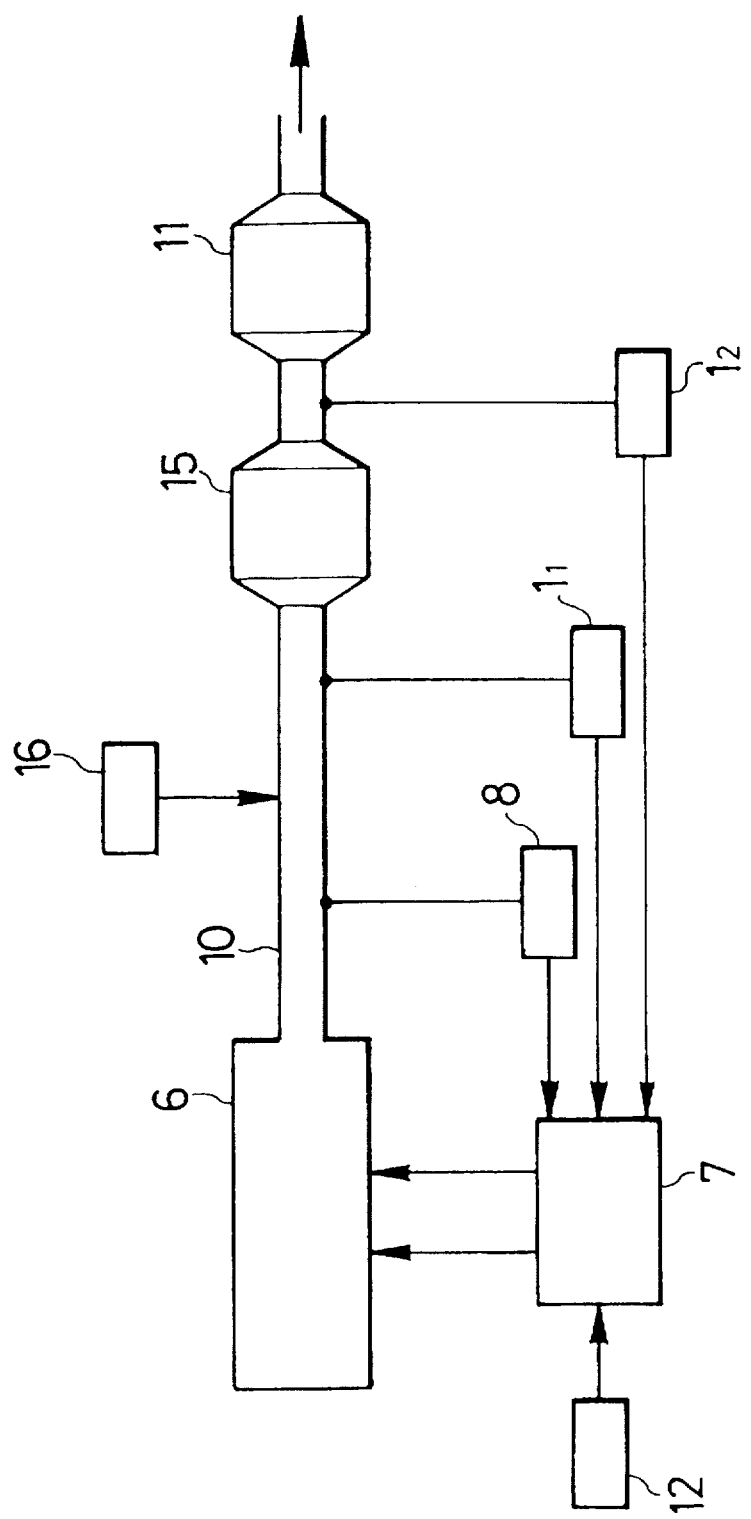
FIG. 16 is a block diagram illustrating an NOx purifying system.

FIG. 16 shows another NOx purifying system. In this NOx purifying system, a lean burn NOx catalyst 15 is disposed in an exhaust pipe 10 upstream of a ternary catalyst 11. An HC supplement source 16 is disposed in the exhaust pipe 10 upstream of a first NOx measuring element $1_1$. Other arrangements are the same as those in the NOx purifying system shown in FIG. 9 and hence, the like reference characters are used to designate portions or components corresponding to those described above.

Figure 17:
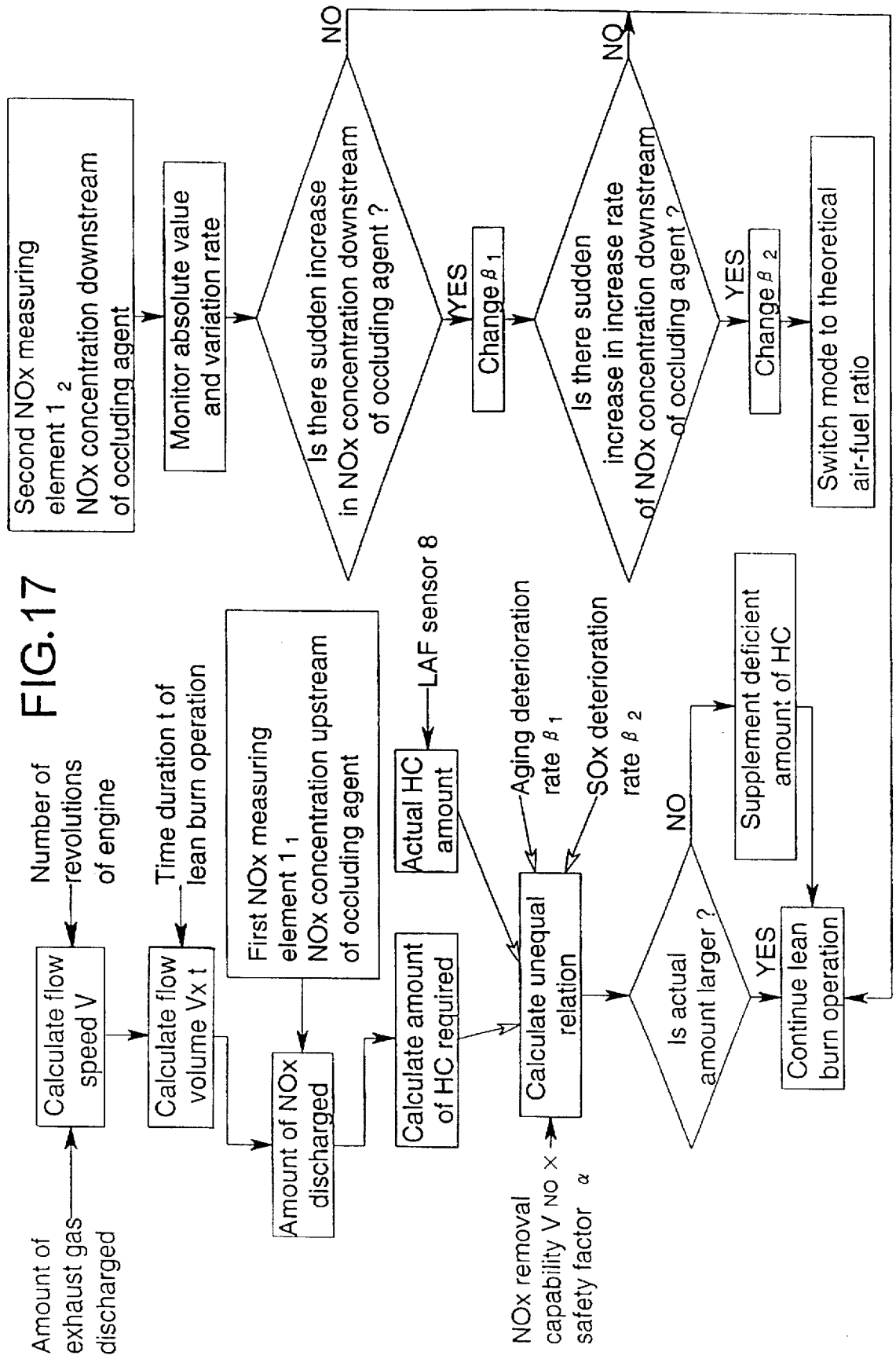
FIG. 17 is a flow chart for an NOx purifying system.

The NOx purifying system shown in FIG. 16 will be described below using the flow chart shown in FIG. 17.

(1) In a lean burn operation, a flow speed V of an exhaust gas is calculated from an amount of exhaust gas discharged and a number of revolutions of an engine.

(2) A flow volume V×t of the exhaust gas is calculated from the flow speed V of the exhaust gas and a time duration t of the lean burn operation.

(3) An amount of NOx discharged, i.e., $C_{NO} \times V \times t$ is calculated based an output from the first NOx measuring element $1_1$, wherein $C_{NO}$ is a concentration of NOx at a location upstream of the lean burn NOx catalyst 15.

(4) An HC amount required for reducing an amount of NOx discharged is calculated. An actual HC amount is calculated based on an output from the LAF sensor 8.

(5) An actual NOx adsorbing capability $V_{NO} \times \alpha \times (\beta_1 + \beta_2)$ of the lean burn NOx catalyst 15 is calculated from an NOx adsorbing capability $V_{NO}$, a safety factor $\alpha$, an aging deterioration rate $\beta_1$ and an SOx deterioration rate $\beta_2$ in the lean burn NOx catalyst 15.

Then, it is determined by calculation whether a relation, $V_{NO} \times \alpha \times (\beta_1 + \beta_2) > C_{NO} \times V \times t$ is established. In order to prevent releasing of NOx from the lean burn NOx catalyst 15, the left and right sides must be in an unequal relationship.

It is determined by calculation whether a relation, actual HC amount > required HC amount, is established between the required HC amount and the actual HC amount. If this unequal relation is not established, it is failed to sufficiently reduce NOx.

(6) If actual HC amount > required HC amount, the lean burn operation is continued.

(7) If actual HC amount > required HC amount, a deficient HC amount is supplemented from the HC supplement source, whereby the lean burn operation is continued.

(8) An absolute value and a variation rate of NOx concentration at a location downstream from the lean burn NOx catalyst is monitored based on an output from the second NOx measuring element $1_2$.

(9) If a sudden increase in NOx concentration at the location downstream from the lean burn NOx catalyst is not produced, the lean burn operation is continued. If the sudden increase in NOx concentration is produced, the aging deterioration rate $\beta_1$ is changed, and the mode is switched to the theoretical air-fuel ratio operation.

(10) If a sudden increase in NOx concentration increase rate at the location downstream from the lean burn NOx catalyst is not produced, the lean burn operation is continued. If the sudden increase in NOx concentration increase rate is produce, the $SO_x$ deterioration rate $\beta_2$ is changed, and the mode is switched to the theoretical air-fuel ratio operation.

A dashed line in FIG. 15 indicates a deterioration situation of the lean burn NOx catalyst 15 by SOx. The deterioration of the lean burn NOx catalyst 15 was measured under the same conditions as those described above. It can ben seen from the dashed line in FIG. 15 that the lean burn NOx catalyst 15 is deteriorated in a short time by SOx.

The converting performance of the lean burn NOx catalyst 15 relies on the HC amount serving as an NOx reducing agent. It is not that the amounts of NOx and HC discharged relative to the air-fuel ratio A/F is equally a certain integral ratio and hence, in any air-fuel ratio A/F range, NOx cannot be always converted.

In a 2-point control at air-fuel ratio values A/F of 14.8 and near 22 as in the existing NOx purifying system, a problem is still not arisen in the NOx removal rate. However, when an engine control is carried out in an air-fuel ratio A/F range of 14.6 to 22 with an enhancement in driveability, it is impossible to sufficiently remove NOx only by an actual HC amount.

In the NOx purifying system shown in FIG. 16, the first NOx measuring element $1_1$ is disposed upstream of the lean burn NOx catalyst 15, so that a sufficient HC amount corresponding to the amount of NOx is supplemented into the exhaust gas, and hence, it is possible to remove NOx in a wide range of air-fuel ratio A/F.

The lean burn NOx catalyst 15 is also deteriorated to a large extent by SOx, as shown by the dashed line in FIG. 15. Therefore, the second NOx measuring element $1_2$ is disposed downstream from the lean burn NOx catalyst 15, so that the level of deterioration of the catalyst 15 is always monitored and hence, it is possible to previously prevent the discharge of NOx. The removing or converting performance of the lean burn NOx catalyst 15 is restored in a reducing atmosphere in the theoretical air-fuel ratio operation, as is the NOx occluding agent 9.

(Third embodiment)

An NOx measuring element 1 having a form similar to that of the NOx measuring element 1 shown in FIG. 1 was produced by the following process:

(a) Ethanol was added to a mixture of 99.5% by weight of $\alpha$-$Nb_2O_5$ (made by Soekawa Chemicals Co., Ltd.) having a purity of 99.9% and 0.5% by weight of ruthenium (Ru) (made by Soekawa Chemicals Co., Ltd.) having a purity of 99.9% and then, the resulting mixture was pulversized at 300 rpm for 3 hours by use of a planetary ball mill.

(b) The mixture powder was subjected to a pressing at 400 kfg/cm² for 5 minutes to form a tablet having a diameter of 10 mm and a thickness of 3 mm.

(c) The tablet was subjected to a sintering at 1,000° C. for 4 hours to provide a tablet-like NOx sensor 5 made of $\beta$-$Nb_2O_5$ and Ru.

(d) Electrodes 3 and 4 are formed by depositing platinum (Pt) on a surface of the NOx sensor 5 by a sputtering process, thereby providing an NOx measuring element 1.

The following measurement of sensitivities of the NOx measuring element 1 to NOx and $O_2$ was carried out:

First, the NOx measuring element 1 heated to 450° C. by a heater was placed into an $N_2$ atmosphere having a temperature of 450° C. to measure an initial resistance $R_N$ by use of a multi-meter. Then, the NOx measuring element 1 heated to 450° C. by the heater was placed into an atmosphere comprising 500 ppm of NOx and the balance of $N_2$ and having a temperature of 450° C., as well as into an atmosphere comprising 500 ppm of $O_2$ and the balance of $N_2$ and having a temperature of 450° C. to measure a resistance value $R_{NO}$ in the atmosphere containing NOx and a resistance value $R_O$ in the atmosphere containing $O_2$ by use of the multi-meter, respectively.

Figure 18:
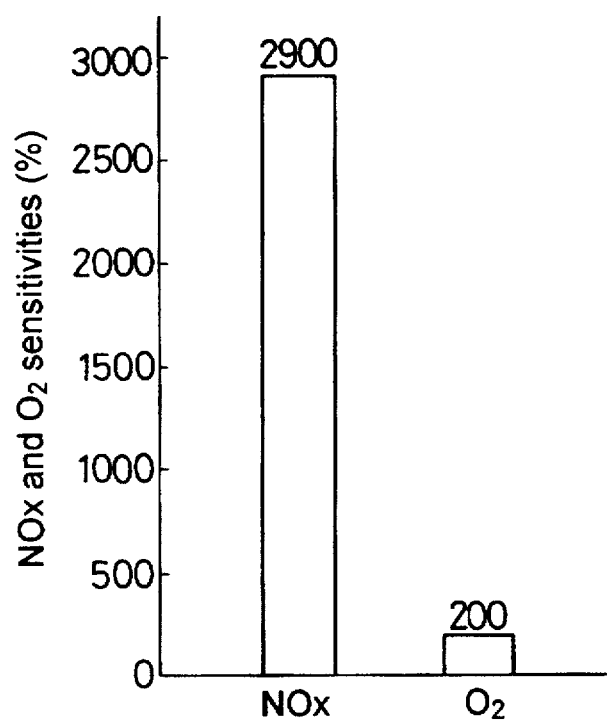
FIG. 18 is a graph illustrating the relationship between the NOx and $O_2$ sensitivities of the NOx sensor.

The sensitivities of the NOx sensor 5 to NOx and $O_2$ were calculated according to the following equations:

NOx sensitivity (%)=$\{(R_{NO}-R_N)/R_N\}\times 100$ $O_2$ sensitivity (%)=$\{(R_O-R_N)/R_N\}\times 100$ FIG. 18 is a graph illustrating the NOx sensitivity and the $O_2$ sensitivity of the NOx measuring element 1. As is apparent from FIG. 18, the NOx measuring element 1 having the NOx sensor 5 made of $\beta$-$Nb_2O_5$ and 0.5% by weight of Ru is higher in NOx sensitivity and lower in $O_2$ sensitivity.

Figure 19:
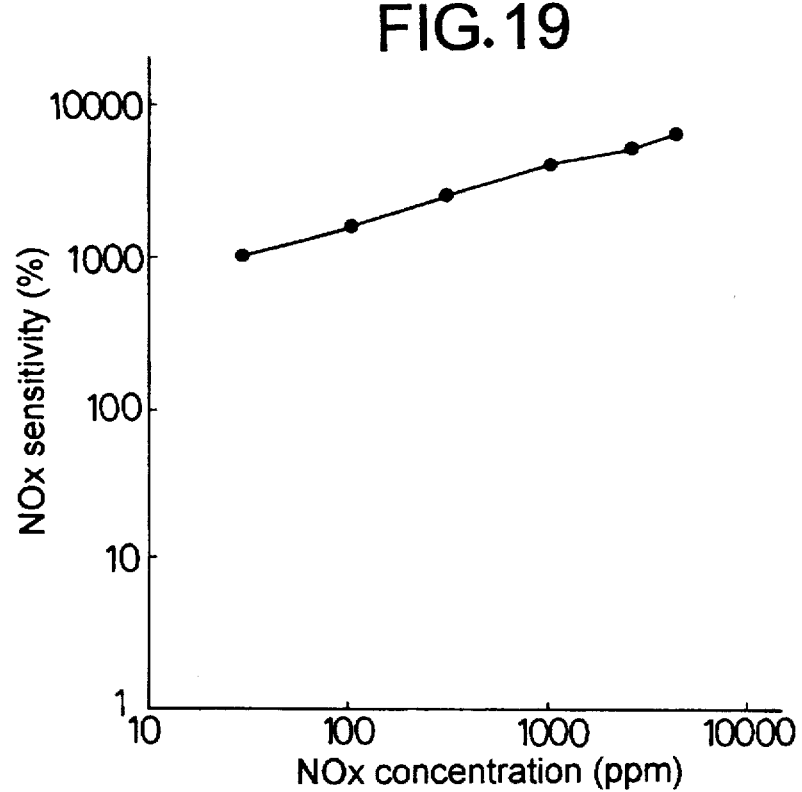
FIG. 19 is a graph illustrating the relationship between the NOx concentration and the NOx sensitivity.

The NOx sensitivity of the NOx sensor 5 was examined under the same conditions as those described above, except that the NOx concentration was varied, thereby providing results shown in FIG. 19. As is apparent from FIG. 19, the NOx sensitivity is enhanced, as the NOx concentration is increased.

Various NO measuring elements 1 were produced in the same process as that described above, except that the content of Ru in the NOx sensor 5 was varied. Using these NOx measuring elements 1, the measurement of a sensitivity to NOx was carried out under the same conditions as those described above, except that the NOx concentration was set at 1,000 ppm, thereby providing results shown in FIG. 20.

Figure 20:
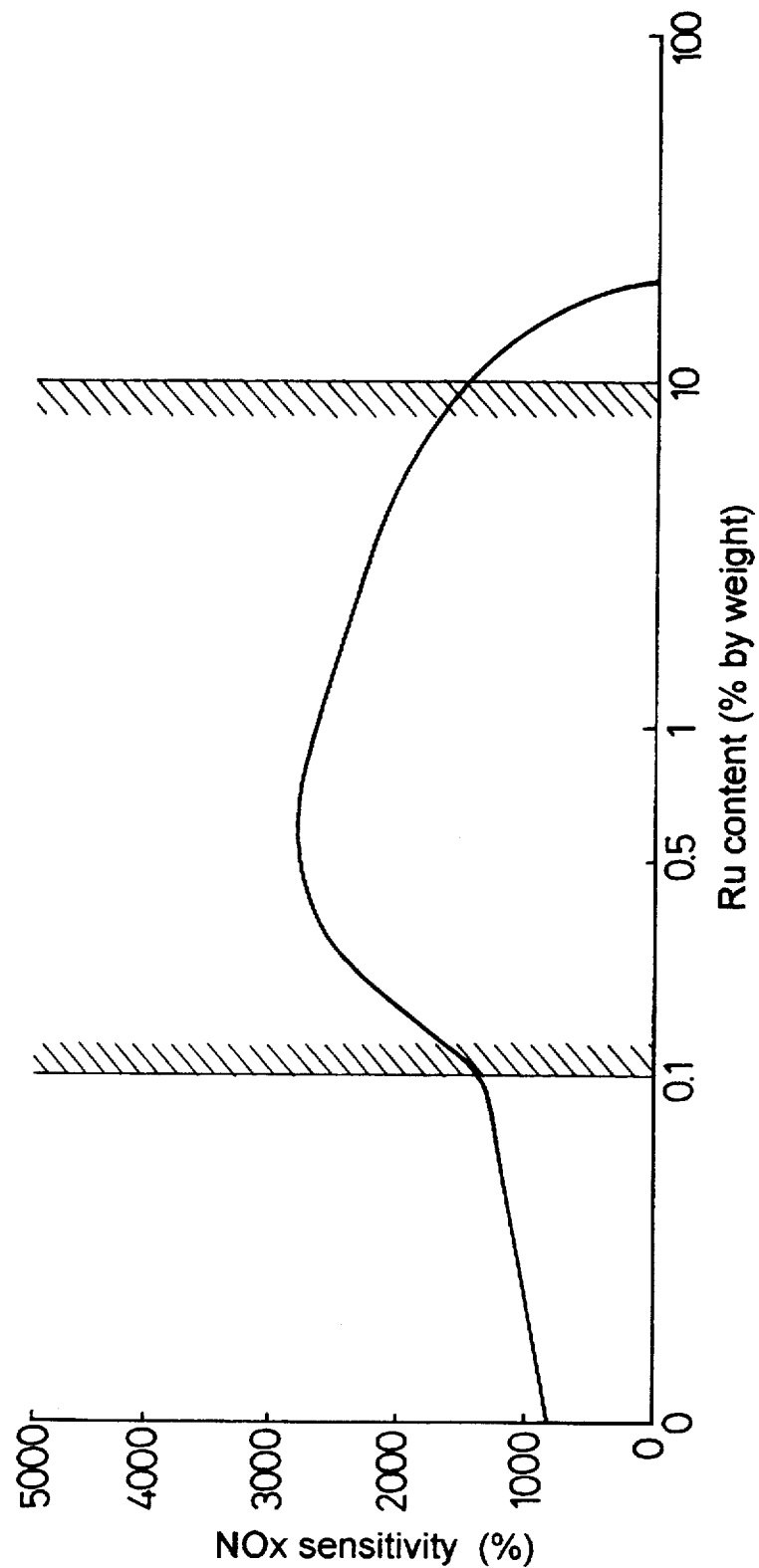
FIG. 20 is a graph illustrating the relationship between the Ru content and the NOx sensitivity.

As is apparent from FIG. 20, if the Ru content is set in a range of 0.1% by weight $\leq$Ru$\leq$10% by weight, the NOx sensitivity $R_{NO}$ can be enhanced.

What is claimed is:

1. An NOx sensor for an exhaust gas exhausted from an internal combination engine, said NOx sensor comprising an NOx measuring element having a surface exposed to the exhaust gas, said surface comprised of a needle crystal aggregate of $\beta$-$Nb_2O_5$, said needle crystal aggregate having needle crystals, adjacent ones of said needle crystals being held in contact with each other, and a pair of electrodes connected to said NOx measuring element for measuring changes in electrical characteristics of said NOx measuring element caused by changes in an NOx content of the exhaust gas.

2. An NOx sensor for an exhaust gas according to claim 1, further comprising an $O_2$ measuring element comprised of $\beta$-$Nb_2O_5$, said $O_2$ measuring element positioned adjacent said NOx measuring and having a surface exposed to the exhaust gas, and a pair of electrodes connected to said $O_2$ measuring element for measuring changes in electrical characteristics of said $O_2$ measuring element caused by changes in an $O_2$ content of the exhaust gas.

3. An NOx sensor for an exhaust gas according to claim 1, wherein said needle crystal aggregate includes $TiO_2$ in an amount of 0.1% by weight $\leq$TiO$\leq$20% by weight.

4. An NOx sensor for an exhaust gas according to claim 1, wherein said needle crystal aggregate includes Ru in an amount of 0.1% by weight $\leq$Ru$\leq$10% by weight.

5. An NOx sensor for an exhaust gas according to claim 1, wherein said needle crystal aggregate of $\beta$-$Nb_2O_5$ is obtained by sintering a granular crystal aggregate of $\alpha$-$Nb_2O_5$ at a sintering temperature of greater than 900° C.

6. An NOx sensor for an exhaust gas according to claim 2, wherein said $O_2$ measuring element includes Cu as a subsidiary component in an amount of 0.1% by atom $\leq$Cu$\leq$10% by atom.

7. An NOx sensor for an exhaust gas according to claim 3, wherein the amount of $TiO_2$ is in a range of 0.5% by weight $\leq$$TiO_2$$\leq$10% by weight.

8. An NOx sensor for an exhaust gas according to claim 4, wherein the amount of Ru is in a range of 0.5% by weight $\leq$Ru 1.0% by weight.

9. An NOx sensor for an exhaust gas, said NOx sensor including an NOx sensing element which comprises a needle crystal aggregate of $\beta$-$Nb_2O_5$ which is obtained by subjecting a granular crystal aggregate of $\alpha$-$Nb_2O_5$ to a thermal treatment.

10. An NOx sensor according to claim 9, wherein thermal treatment comprising: (a) heating said granular crystal aggregate of $\alpha$-$Nb_2O_5$ at a first temperature for a first predetermined period of time wherein said first temperature is less than a transformation temperature of about 900° C., said transformation temperature converting said granular crystal aggregate of α-Nb$_2$O$_5$ to said needle crystal aggregate of β-Nb$_2$O$_5$ , and (b) heating said granular crystal aggregate of α-Nb$_2$O$_5$, to a second temperature for a second predetermined period of time, said second temperature being greater than said transformation temperature of about 900° C. to convert said granular crystal aggregate of α-Nb$_2$O$_5$ to said needle crystal aggregate of β-Nb$_2$O$_3$ crystals.

11. An NOx sensor for an exhaust gas, said NOx sensor including an NOx sensing element which comprises a needle crystal aggregate of β-Nb$_2$O$_5$ including TiO$_2$ as a subsidiary component, the needle crystal aggregate of β-Nb$_2$O$_5$ and TiO$_2$ being obtained by subjecting a mixture of a granular crystal aggregate of α-Nb$_2$O$_5$ and TiO$_2$ to a thermal treatment comprising: (a) heating said granular crystal aggregate of α-Nb$_2$O$_5$ and TiO$_2$ at a first temperature for a first predetermined period of time wherein said first temperature is less than a transformation temperature of about 900° C., said transformation temperature converting said granular crystal aggregate of α-Nb$_2$O$_2$ to said needle crystal aggregate of β-Nb$_2$O$_5$; and (b) heating said granular crystal aggregate of α-Nb$_2$O$_5$ and TiO$_2$ to a second temperature for a second predetermined period of time, said second temperature being greater than said transformation temperature of about 900° C. to convert said granular crystal aggregate of α-Nb$_2$O$_5$ to said needle crystal aggregate of β-Nb$_2$O$_5$.

12. An NOx sensor according to claim 11, wherein TiO$_2$ is included in said needle crystal aggregate of β-Nb$_2$O$_5$ in an amount of 0.5% by weight ≦TiO$_2$≦10% by weight.

13. An NOx sensor for an exhaust gas exhausted from an internal combustion engine, said NOx sensor including an NOx sensing element which comprises a needle crystal aggregate of β-Nb$_2$O$_5$, and an O$_2$ sensing element which comprises β-Nb$_2$O$_5$ said O$_2$ sensing element being adjacent said NOx sensing element, and means connected to said NOx sensing element and said O$_2$ sensing element for separately measuring electrical resistances of said NOx sensing element and said O$_2$ sensing element, said means calculating an electrical resistance correction value based on the electrical resistance of said O$_2$ sensing element, and wherein said means subtracts said electrical resistance correction value from the electrical resistance of said NOx sensing element to determine NOx in the exhaust gas.

14. An NOx sensor according to claim 13, wherein said O$_2$ sensing element includes Cu as a subsidiary component in an amount of 0.1% by atom ≦Cu≦10% by atom.

15. A method for producing an NOx sensing element for an NOx sensor for an exhaust gas, said NOx sensing element comprising a needle crystal aggregate of β-Nb$_2$O$_5$ and TiO$_2$ as a subsidiary component, the method comprising:

preparing a mixed material of a granular crystal aggregate of α-Nb$_2$O$_5$ and TiO$_2$;

subjecting the mixed material to a thermal treatment comprising: (a) heating said granular crystal aggregate of α-Nb$_2$O$_5$ and TiO$_2$ at a first temperature for a first predetermined period of time, wherein said first temperature is less than a transformation temperature of 900° C., said transformation temperature converting said granular crystal aggregate of α-Nb$_2$O$_5$ to said needle crystal aggregate of β-Nb$_2$O$_5$; and (b) heating said granular crystal aggregate of α-Nb$_2$O$_5$ and TiO$_2$ at a second temperature for a second predetermined period of time, said second temperature being greater than said transformation temperature of about 900° C. to convert said granular crystal aggregate of α-Nb$_2$O$_5$ to said needle crystal aggregate of β-Nb$_2$O$_5$.

* * * * *

UNITED STATES PATENT AND TRADEMARK OFFICE
CERTIFICATE OF CORRECTION

PATENT NO. : 5,800,783
DATED : September 1, 1998
INVENTOR(S) : Nanaumi et al.

It is certified that error appears in the above-identified patent and that said Letters Patent is hereby corrected as shown below:

Column 12,
Line 32, after "measuring" insert -- element --.
Line 39, delete "TiO" and substitute -- $TiO_2$ --.

Column 14,
Line 24, after "of" insert -- about --.

Signed and Sealed this

Eighteenth Day of June, 2002

Attest:

JAMES E. ROGAN
Attesting Officer     Director of the United States Patent and Trademark Office